United States Patent [19]
Logeman

[11] Patent Number: 5,792,141
[45] Date of Patent: Aug. 11, 1998

[54] ELECTROSURGICAL DEVICE FOR PREVENTING CAPACITIVE COUPLING AND THE FORMATION OF UNDESIRABLE CURRENT PATHS

[75] Inventor: John Logeman, Park Ridge, Ill.

[73] Assignee: MediCor Corporation, Wheeling, Ill.

[21] Appl. No.: 611,041

[22] Filed: Mar. 5, 1996

[51] Int. Cl.$^6$ .................................................. A61B 17/39
[52] U.S. Cl. .................................................. 606/46; 606/41
[58] Field of Search .................... 606/41, 42, 45–52

[56] References Cited

U.S. PATENT DOCUMENTS

| | | |
|---|---|---|
| 3,707,149 | 12/1972 | Hao et al. . |
| 3,933,157 | 1/1976 | Bjurwill et al. . |
| 4,184,492 | 1/1980 | Meinke et al. ........................... 606/46 |
| 4,200,104 | 4/1980 | Harris . |
| 4,494,541 | 1/1985 | Archibald . |
| 4,615,330 | 10/1986 | Nagasaki et al. . |
| 4,617,927 | 10/1986 | Manes . |
| 4,844,063 | 7/1989 | Clark . |
| 5,087,257 | 2/1992 | Farin et al. . |
| 5,312,401 | 5/1994 | Newton et al. ........................... 606/46 |

FOREIGN PATENT DOCUMENTS

WO 94/22383  10/1994  WIPO .

OTHER PUBLICATIONS

Tucker et al, "Capacitive Coupled Stray Currents . . . Electrosurgical Procedures", Biomedical Instrumentation and Technology, vol. 26, pp. 303–311, 1992.

*Primary Examiner*—Michael Peffley
*Attorney, Agent, or Firm*—Olson & Hierl, Ltd.

[57] ABSTRACT

A monopolar electrosurgical device suitable for cutting and/or coagulation of tissue is described. The device includes a trocar assembly and a probe assembly. The trocar assembly has an insulated portion and a conductive guide portion. The conductive guide portion defines a passage with the probe assembly slidably received therein. The probe assembly includes a conductive probe with a proximal end and a distal end. Surrounding the probe is an insulation layer which extends from the distal end of the probe. Attached to the insulation layer and also surrounding the probe is a conductive shield. The conductive shield is electrically connected to the conductive guide portion of the trocar assembly.

21 Claims, 5 Drawing Sheets

5,792,141

1

ELECTROSURGICAL DEVICE FOR PREVENTING CAPACITIVE COUPLING AND THE FORMATION OF UNDESIRABLE CURRENT PATHS

FIELD OF THE INVENTION

The present invention relates to electrosurgical devices, and in particular to a monopolar electrosurgical device having a probe extending through a trocar wherein the likelihood of capacitive coupling and the formation of undesirable current paths is minimized.

BACKGROUND OF THE INVENTION

Systems which use high frequency electrical current for cutting and/or coagulation of human tissue are well known in the art. Normally, the electrical current is applied to preselected tissue by using a probe. The probe is energized by an electrosurgical generator. The current emanating from the probe destroys the preselected tissue by producing a high temperature region around the probe tip. The current flows back to the electrosurgical generator by means of a return electrode which is connected to the patient.

Referring to FIG. 1, a schematic and an enlarged cross-sectional side view is provided of a prior art system 10 for cutting and/or coagulation of tissue with high frequency electrical current. As stated previously, the system 10 includes an electrosurgical generator 12, a return electrode 14, and a cylindrical electrode probe 16 which is slidably received within a metallic trocar sheath or cannula 18. The probe 16 is surrounded by insulation material 20 which extends from the probe tip 22 and through the trocar sheath 18.

The probe 16 is connected, via lead 24, to the output terminal of the generator 12. The generator 12 is of a conventional type with the return terminal of the generator being connected, via lead 26, to the return electrode 14.

While the prior art system 10 is effective for cutting and/or coagulation of human tissue, the use of such a system can also cause several serious problems.

For example, conductive elements positioned around the probe 16 can become charged. The charging is caused by the current flowing through the probe 16 and a dielectric (i.e., insulation 20) which is positioned between the probe and any other conductive elements such as the metallic trocar 18. The charging of the conductive elements around the probe is commonly known as the capacitive effect.

Correspondingly, the charged elements will dissipate their energy in the form of stray current. The current will flow through either a path in the patient's body or through any other readily available ground return path.

As the stray current flows through a patient's body, the current can cause severe damage. For example, current from the charged trocar 18 can cause severe burns as it travels back through the patient's body and towards the return electrode 14. The resulting burns can range from minor damage to the skin surrounding the area where the trocar 18 attaches to the patient, to severe burns on organs such as the bowel.

Personnel who come into contact with any of the charged metallic structures may also be burned as the stray current passes through their body and to a ground potential. As indicated above, the trocar 18 can build up a significant charge. In such an event, the energy within the trocar 18 will be dissipated through the patient and anyone who comes into contact with it.

2

Personnel who come into contact with the trocar 18 also provide an alternative ground return path for the current being emitted from the probe tip 22. Therefore, severe damage to a patient may occur as the current utilizes the alternative ground return path provided by the "grounded" trocar 18.

Correspondingly, the present invention provides a device which overcomes or at least minimizes the above-discussed problems by reducing the likelihood of undesirable capacitive coupling and the formation of undesirable current paths.

SUMMARY OF THE INVENTION

The present invention provides a monopolar electrosurgical device that minimizes the likelihood of capacitive coupling and the formation of undesirable alternate current paths while high frequency electrical current is used in a surgical procedure to destroy preselected tissue.

The device embodying the present invention is especially suitable for directing high frequency electrical current to preselected regions within a patient. Capacitive coupling of conductive elements, such as the trocar, is minimized. Furthermore, the present device reduces the likelihood that the trocar will provide an alternate path for the return of electrical current delivered within the body of a patient.

The electrosurgical device embodying the present invention includes a trocar assembly and a probe assembly. The trocar assembly has an insulated portion and a conductive guide portion. The conductive guide portion forms a passage for the probe assembly which is slidably received therein. The probe assembly includes a conductive probe with a proximal end and a distal end. Surrounding the probe is an insulation layer which extends from the distal end of the probe. Attached to the insulation layer and also surrounding the probe is a conductive shield. The conductive shield is conductively associated with the conductive guide portion of the trocar assembly.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

The present invention provides a monopolar electrosurgical device which minimizes the likelihood of capacitive coupling and the formation of undesirable current paths while using high frequency electrical current to destroy preselected tissue within a patient. The electrosurgical device includes a trocar assembly and a probe assembly. The trocar assembly has an insulated portion and a conductive guide portion associated therewith. The probe assembly is slidably received within a passage defined by the conductive guide portion of the trocar assembly. The probe assembly includes a conductive probe with a proximal end and a distal end. Surrounding the probe is an insulation layer which extends from the distal end of the probe toward the proximal end of the probe. A conductive shield surrounds at least a portion of the probe and is a part of the probe assembly. The conductive shield is part of a conductive path that includes the conductive guide portion of the trocar assembly.

Figure 1:
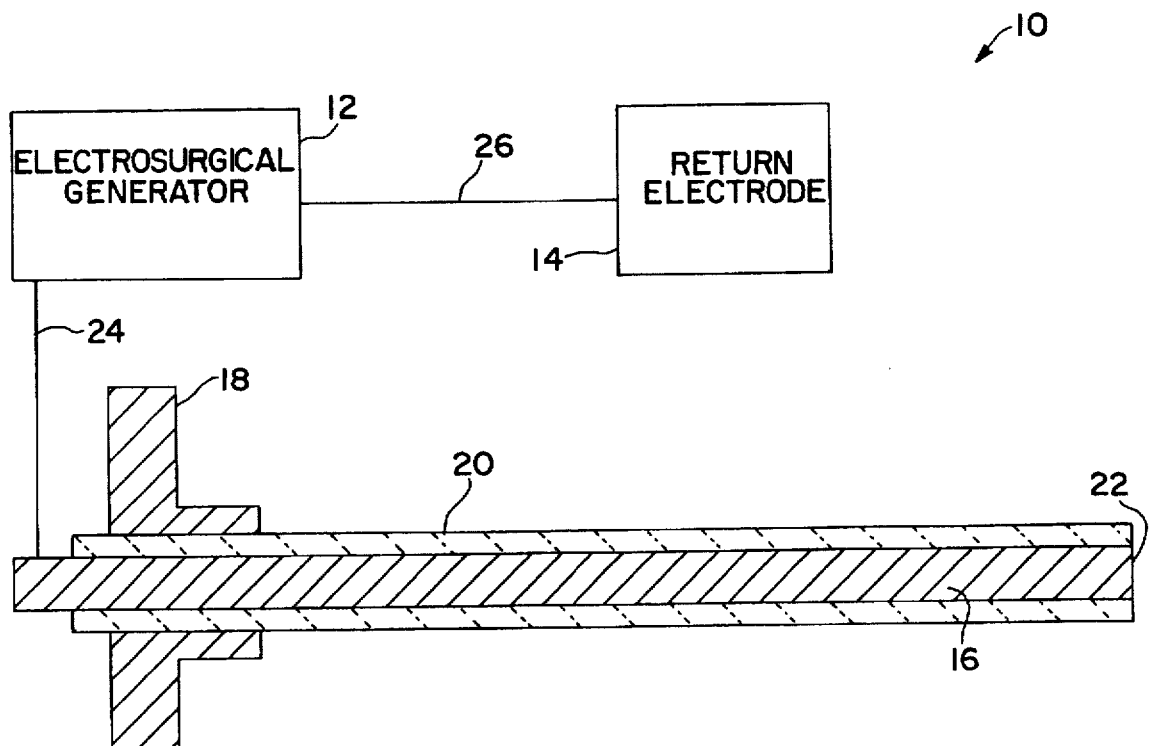
FIG. 1 is a schematic, enlarged cross-sectional side view illustrating a prior art system for cutting and/or coagulation of tissue with high frequency electrical current.
Figure 2:
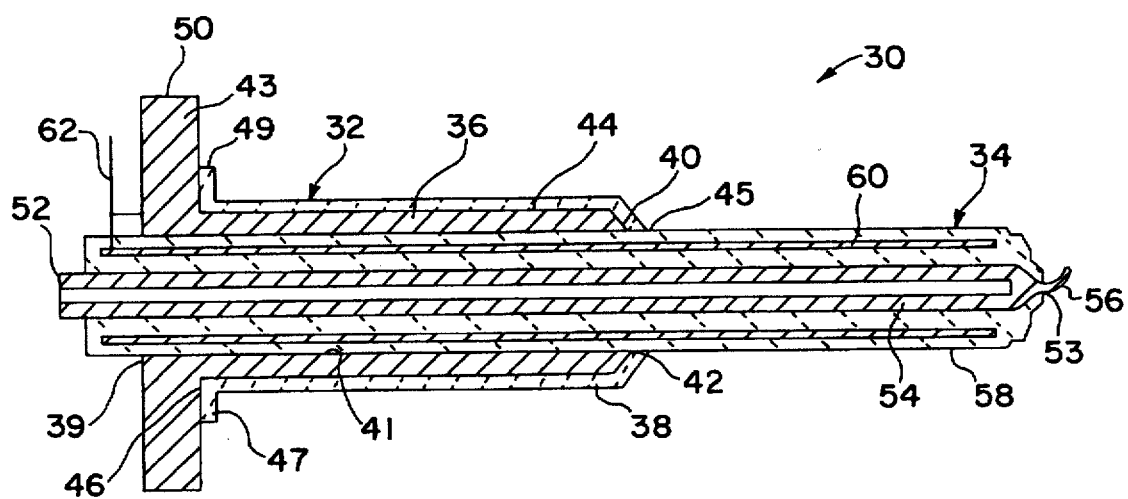
FIG. 2 is an enlarged cross-sectional side view of an electrosurgical device in accordance with the present invention.

Referring to the drawings, and particularly to FIG. 2, a monopolar electrosurgical device 30 includes a trocar assembly 32 and a probe assembly 34.

The trocar assembly 32 has a conductive guide 36 which is partially surrounded by an insulation layer 38. The conductive guide 36 can be made of a conductive material such as a metal or a metal alloy. A typical material of construction from the conductive guide 36 is stainless steel. Conversely, the insulation layer 38 is made of an insulating material such as a plastic material or a ceramic material having the appropriate dielectric properties.

The conductive guide 36 is generally tubular in shape with a probe receiving proximal end 39, an open distal end 40, and an open passage 41 extending therebetween. The open distal end 40 of the guide 36 is tapered to form a pointed tip 42 around the opening of the passage 41. Furthermore, extending radially outwardly from the probe receiving proximal end 39 of the guide 36 is a flange 43 that surrounds open passage 41.

Encasing the outside surface 44 of the conductive guide 36 is the insulation layer 38. The insulation layer 38 extends from the open distal end 40 of the conductive guide 36 to the flange 43 and can cover a portion of the flange 43 as well. The insulation layer 38 generally conforms to the shape of outside surface 44 and provides a pointed end 45 as well as a flanged end 46 which abuts the flange 43 of the conductive guide 36. As shown in FIG. 2, the outside diameter 49 of the insulation flange 47 is less than the outside diameter 50 of the conductive flange 43.

However, in other embodiments, the outer diameter of the insulation flange can be equal to, or larger than, the outside diameter of the conductive flange.

Slidably received within the trocar assembly passage 41 is the probe assembly 34. The probe assembly 34 has a proximal end 52 and a distal end 53 which, respectively, protrude from the probe receiving proximal end 39 and the pointed end 45 of the trocar assembly 32. Extending along the center of the probe assembly 34 is a conductive probe 54. The probe 54 is generally tubular in construction, made of a conductive material which can be a metal, a metal alloy, or the like, and has an electrode, such as a curved tip 56 protruding from the distal end 53. The probe electrode can have other shapes such as straight or blunted, as is well known in the electrosurgery art.

Surrounding the probe 54 is an insulation layer 58. The insulation layer 58 can be a plastic material, a ceramic material, or a composite having the appropriate dielectric properties. The insulation layer 58 is generally tubular in shape and covers probe 54 substantially along its entire length from the distal end 53 to the proximal end 52. Thus, only the probe tip 56 and the proximal end 52 of the probe 54 project from under the insulation layer 58.

Embedded within the probe insulation layer 58 is lead 62 and a conductive shield 60 made of a conductive material such as a metal or a metal alloy. The shield 60 is cylindrical and in this particular embodiment extends substantially the entire length of the body of probe 54 from the proximal end 52 to the distal end 53 of the probe. The shield 60 does not contact the probe 54 because of the insulation 58 between the probe 54 and the shield. Lead 62 provides a conductive path from the shield 60 to the trocar assembly 32 and to the return terminal of an electrosurgical generator.

The lead 62 is electrically connected to the shield 60 and extends through the insulation 58 to the conductive guide portion 36 of the trocar assembly 32.

Figure 3:
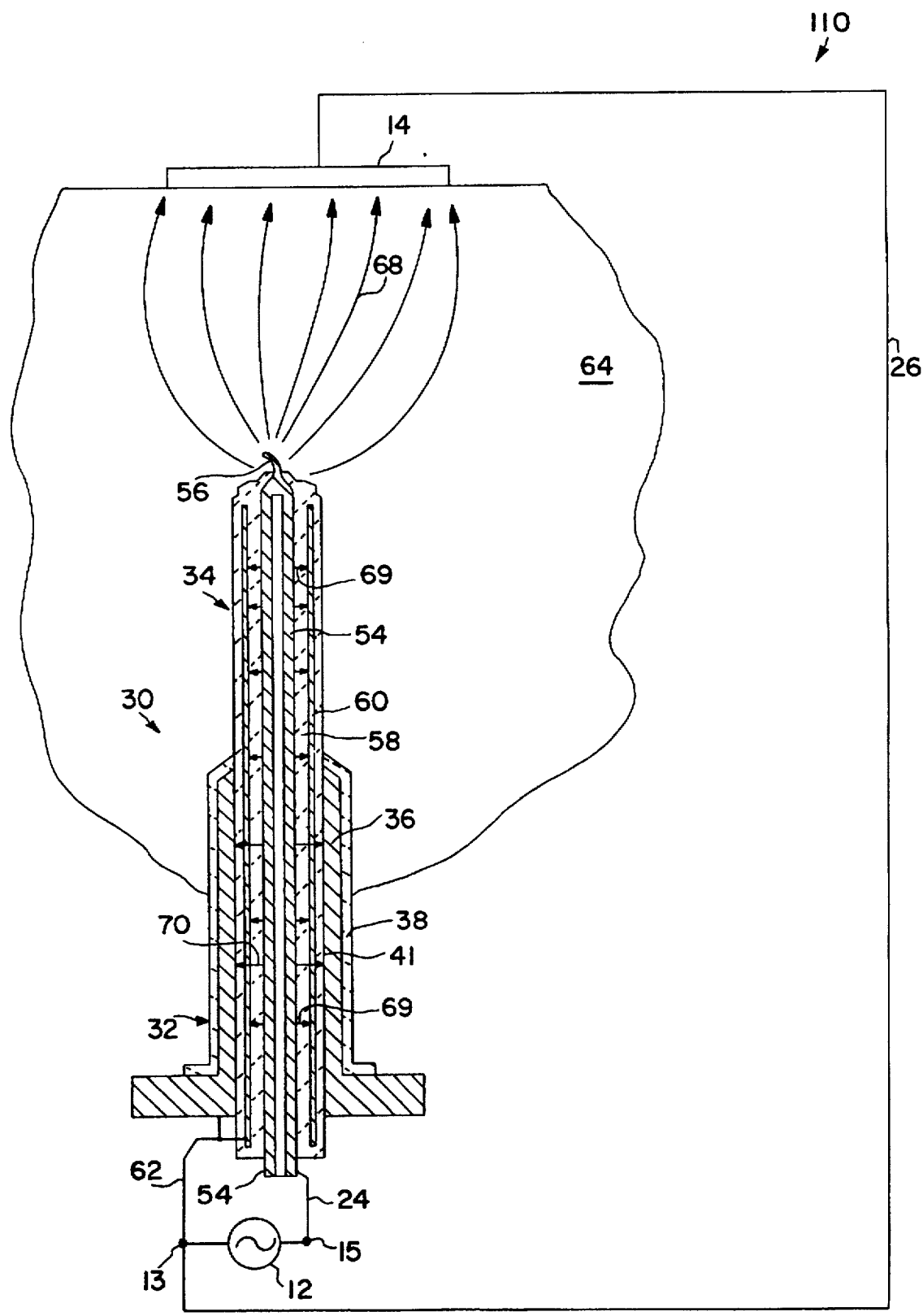
FIG. 3 is a schematic, enlarged cross-sectional side view illustrating the electrosurgical device of FIG. 2 within a system for cutting and/or coagulation of the tissue of a patient.

Turning to FIG. 3, the monopolar electrosurgical device 30 of FIG. 2 is shown within a system 110 for cutting and/or coagulation of tissue 64 within a patient. As stated previously, the return electrode 14 is attached to the patient and, via lead 26, to the return terminal 13 of the electrosurgical generator 12. Likewise, the lead 62 extending from both the trocar assembly 32 and the probe assembly 34 is operably connected to the return terminal 13 of the electrosurgical generator 12. Finally, the output terminal 15 of the electrosurgical generator 12 is operably connected, via lead 24, to the electrode probe 54.

High frequency electrical current produced by the generator 12 passes through the probe 54 and is emitted from the probe tip 56. The current 68 then continues through patient's tissue 64 and into the return electrode 14 where it travels back to the generator 12.

As shown in FIGS. 2 and 3, the conductive guide 36 of the trocar 32 provides a controlled current return path to the generator 12 for any stray current because the trocar is connected, via lead 62, to the return terminal 13 of the generator. However, the conductive guide 36 does not provide an alternative return path for the principal electrical current 68 emanating from the tip 56 of the probe 54 because of the insulation 38 between the conductive guide 36 and any tissue of the patient. Therefore, the insulation 38 also does not provide an undesirable and uncontrollable resistive current path between the probe 54 and the trocar assembly 32.

As indicated previously, the high frequency electrical current passing through the probe 54 and the dielectric provided by the insulation 58 enshrouding the probe, generates in an electrostatic field 69 that is emitted radially along the entire length of the probe. This field 69 can cause capacitive coupling between the probe 54 and other conductive elements situated around the probe.

As the electrostatic field 69 emanates from the probe 54, however, the field energy is absorbed by the shield 60 and conveyed, via lead 62, into the return terminal 13 of the generator 12. Therefore, any conductive elements positioned around the electrosurgical device 30 are not capacitively coupled since the electrostatic field 69 emanating from the probe 54 is absorbed by the conductive shield 60.

Any portion of the field 69 that may escape (i.e., leak) from the shield 60 is radiated along the length of the probe assembly 34. Correspondingly, any such electrostatic field 70 due to leakage within the trocar passage 41 strikes the conductive guide 36. Thus, such field energy is also absorbed by the conductive guide 36 and bled off, via lead 62, into the return terminal 13 of the generator 12. In this manner, the trocar 32 does not become charged due to capacitive coupling because all electrostatic energy striking the trocar is bled off into the return terminal 13 of the generator 12.

Figure 4:
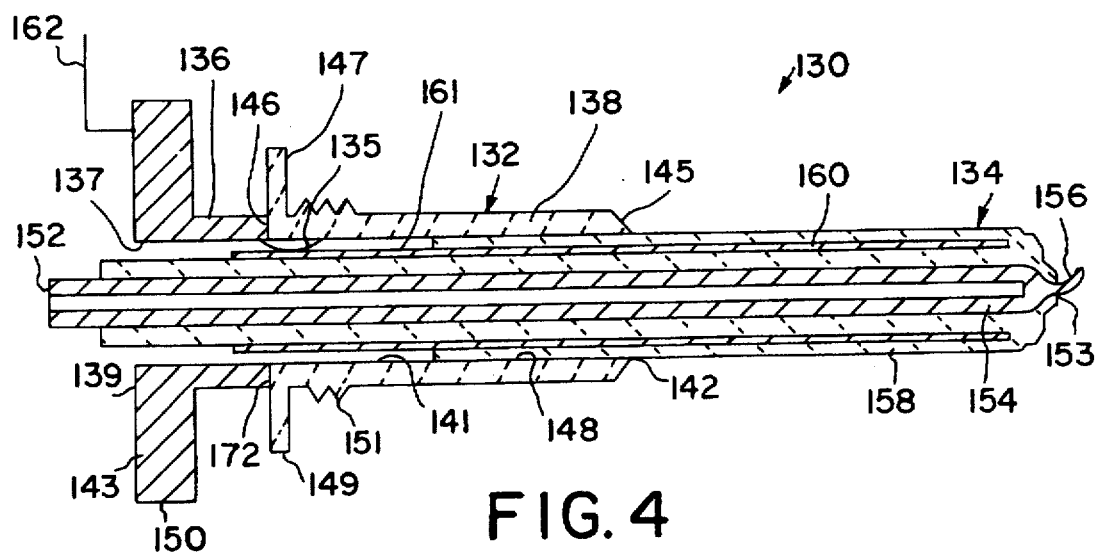
FIG. 4 is an enlarged cross-sectional side view of an electrosurgical device embodying the present invention.

FIG. 4 shows another embodiment of the present invention. Electrosurgical device 130 includes a trocar assembly 132 and a probe assembly 134.

The trocar assembly 132 has a conductive guide 136 which is generally tubular in shape with a probe receiving proximal end 139, a distal end 172, and a bore 137 extending therebetween. The conductive guide 136 is made of a conductive material such as a metal or a metal alloy. Extending radially outwardly from the probe receiving proximal end 139 of the guide 136 is a conductive flange 143.

Attached to the distal end 172 of the conductive guide 136 is an insulated guide 138. Like the conductive guide 136, the insulated guide 138 is generally tubular in shape with a proximal end 146, a pointed end 145, and a bore 148 extending therebetween. The insulated guide 138 is made of dielectric material such as a plastic or a ceramic. The pointed end 145 of the insulation guide 138 is tapered to form a pointed tip 142 around the opening of the bore 148. In addition, flange 147 is provided at the proximal end 146 of the guide 138 and extends outwardly therefrom. The outer diameter 149 of the insulated flange 147 is less than the outer diameter 150 of the conductive flange 143.

The insulated guide 138 also can have threads 151 around the outside of the guide and adjacent to the flange 147 if desired. Such threads can provide a means for securing the trocar assembly 132 to a patient.

The bore 137 within the conductive guide 136 and the bore 148 within the insulation guide 138 are aligned axially such that an open passage 141 is provided from the probe receiving proximal end 139 of the trocar assembly 132 to the pointed end 145.

Extending within the trocar passage 141 is a conductive strip 135 which serves as a contact with conductive shield 160 described hereinbelow. The conductive strip 135 is made of a resilient conductive metal and is attached to the conductive guide 136. The conductive strip 135 extends from the conductive portion 136 to the insulated guide 138 of the trocar assembly 132.

Received within the trocar passage 141 is the probe assembly 134. The probe assembly 134 has a proximal end 152 and a distal end 153 which, respectively, protrude from the probe receiving proximal end 139 and the pointed end 145 of the trocar assembly 132. Extending along the center of the probe assembly 134 is a conductive probe 154. The probe 154 is generally tubular in construction, made of a conductive material such as a metal or a metal alloy, and has a curved tip electrode 156 protruding from the distal end 153.

Surrounding the probe 154 is an insulation layer 158. The insulation layer 158 can be a plastic material or a ceramic material. The insulation layer 158 is generally tubular in shape and covers the probe 154 from the distal end 153 to the proximal end 152. Thus, only the probe tip 156 and the proximal end 152 of the probe 154 project from the insulation 158.

Partially embedded within the probe insulation 158 is a conductive shield 160 made of a suitable conductive material. The shield 160 is cylindrically shaped and extends from within trocar assembly 132 to the distal end 153 of the probe. The shield 160 is partially embedded within the insulation 158 such that it does not contact the probe 154. However, an exposed portion 161 of the shield protrudes from the insulation 158 and is contained within the trocar passage 141 adjacent to the proximal end 152 of the probe assembly 134.

Pressing against the exposed portion 161 of the shield 160 and in electrical contact therewith is the conductive strip 135. As the probe assembly 134 slides within the trocar passage 141, the strip 135 remains in electrical contact with the shield 160. Correspondingly, the conductive strip 135 provides a conductive path from the shield 160 to the conductive portion 136 of the trocar assembly 132. Furthermore, a lead 162 connects the conductive portion 136 of the trocar assembly 132 to the return terminal of an electrosurgical generator.

In preparation for use in an electrosurgical procedure, the trocar 132 is attached to a patient such that the flange 147 abuts against the patient. In addition, the return electrode, such as electrode 14 in FIG. 3, is attached to both the patient and the electrosurgical generator return terminal. Likewise, the lead 162 extending from the trocar assembly 132 is connected to the generator return terminal. Finally, the generator output terminal is connected to the electrode probe 154.

During the electrosurgical procedure, the high frequency electrical current produced by the generator is passed through the probe 154 and is emitted from the probe tip 156. However, the electrical current emanating from the tip 156 of the probe 154 cannot use the conductive guide 136 as a resistive return path because of the insulation 138 between the conductive guide and the patient. Therefore, an undesirable resistive current path from the probe 154 to the trocar assembly 132 can be avoided.

The high frequency electrical current passing through the probe 154 and the dielectric provided by the insulation 158 enshrouding the probe, results in an electrostatic field that is emitted radially along the entire length of the probe. As the electrostatic field emanates from the probe 154, however, it strikes the conductive shield 160. Consequently, the field energy is absorbed by the shield 160 and conveyed, via the conductive strip 135, the conductive guide 136, and the lead 162, into the return terminal of the generator. Therefore, any conductive elements positioned around the electrosurgical device 130 do not become capacitively coupled since the electrostatic field emanating from the probe 154 is absorbed by the conductive shield 160.

Furthermore, any portion of the field which comes into contact with the conductive guide 136 is absorbed by the guide and bled off, via lead 162, into the return terminal of the generator. Therefore, the trocar 132 does not become charged due to capacitive coupling because all stray electrostatic energy is bled off into the return terminal of the generator.

Figure 5:
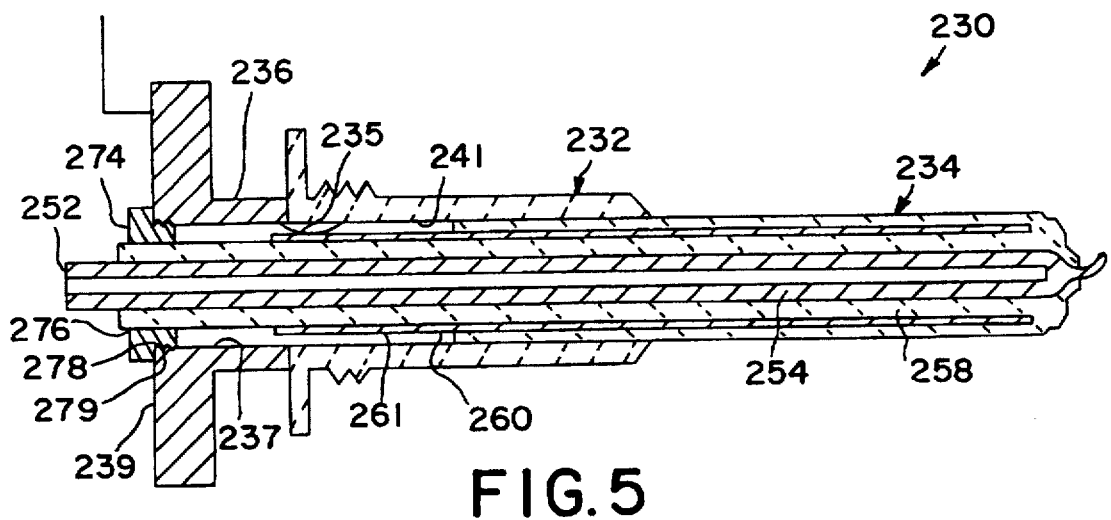
FIG. 5 is an enlarged cross-sectional side view of a further embodiment of the present invention.

Turning to FIG. 5, an enlarged cross-sectional side view is provided of another embodiment of an electrosurgical device 230 in accordance with the present invention. The electrosurgical device 230 is similar to the electrosurgical device 130 depicted in FIG. 4 except for the cap 274 attached to the conductive portion 236 of the trocar assembly 232. In FIG. 5, in the 200-series of numerals the last two digits depict structural elements that are similar in function to those described hereinabove and having numerals with the same last two digits.

The cap 274 is disk shaped with a bore 276 extending through its center. Located around the periphery of the cap 274 is an indented portion 278 which is threaded and mates to complementary threads 279 situated around the trocar passage 241 and adjacent to the probe receiving proximal end 239.

As shown in FIG. 5, the cap bore 276 has a diameter which is smaller than that of the cylindrical shield 260. Therefore, only the probe 254 and the surrounding insulation 258 can slide through the bore 276.

The cap 274 prevents the exposed portion 261 of the shield 260 from protruding from the trocar passage 241. In addition, the cap 274 keeps the proximal end 252 of the probe assembly from being extended too far from the trocar assembly 232. In this manner the electrical connection between the strip contact 235 and the exposed portion 261 of the shield 260 can be maintained at all times during the use of the electrosurgical instrument.

Figure 6:
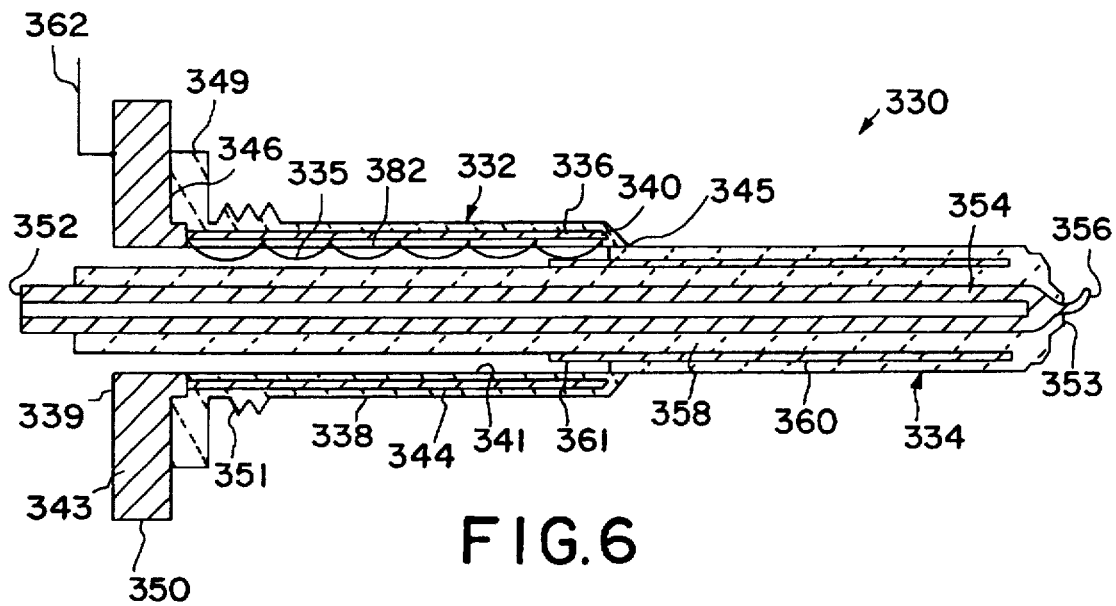
FIG. 6 is an enlarged cross-sectional side view of yet another electrosurgical device in accordance with the present invention.

Referring to FIG. 6, an enlarged cross-sectional side view of yet another embodiment of an electrosurgical device 330 in accordance with the present invention is depicted. The device 330 includes a trocar assembly 332 and a probe assembly 334.

The trocar assembly 332 has a conductive guide 336 which is partially surrounded by an insulation layer 338. The conductive guide 336 is made of a conductive material such as a metal or a metal alloy. Conversely, the insulation layer 338 is made of an insulating material such as a plastic, a ceramic, or a composite.

The conductive guide 336 is generally tubular in shape with a probe receiving proximal end 339, an open distal end 340, and an open passage 341 extending therebetween. Furthermore, radially extending from the probe receiving proximal end 339 of the guide 336 is a flange 343. Partially encasing the outside 344 of the conductive guide 336 and advancing within the trocar passageway 341 is the insulation layer 338. The portion of the insulation layer 338 on the outside 344 of the guide 336 extends over the open distal end 340 of the guide 336 and to the flange 343. Likewise, the portion of the insulation layer 338 within the passage 341 extends from the open distal end 340 of the guide and towards the probe receiving proximal end 339. Correspondingly, the insulation layer 338 is a tubular envelope with a pointed end 345 and a flanged end 346 which abuts against the flange 343 of the conductive guide 336. As shown in FIG. 6, the outer diameter 349 of the insulation flange 347 is less than the outer diameter 350 of the conductive flange 343.

The insulation layer 338 also can have threads 351 around the outside and adjacent to the flange 347. As stated hereinabove, the threads can provide a means for attaching the trocar assembly 332 to a patient if desired.

That portion of the insulation material 338 which extends within the trocar passage 341 defines a channel 382 which allows access from within the passage 341 to the conductive guide 336. Thus, the channel 382 extends from the open distal end 340 and towards the probe receiving proximal end of the guide 336.

Connected to the conductive guide 336 and extending from the channel 382 and into the trocar passage 341 is a conductive strip 335. The conductive strip 335 is made of a resilient conductive metal and can be, as shown in FIG. 6, attached to the conductive guide 336 at spaced intervals along the strip.

Received within the trocar passage 341 is the probe assembly 334. The probe assembly 334 has a proximal end 352 and a distal end 353 which, respectively, protrude from the probe receiving proximal end 339 and the pointed end 345 of the trocar assembly 332. Conductive probe 354 extends along the center of the probe assembly 334. The probe 354 is generally tubular in construction, made of a conductive material such as a metal or a metal alloy, and has a curved electrode tip 356 protruding from the distal end 353.

An insulation layer 358 surrounds the probe 354. The insulation layer 358 can be a plastic material or a ceramic material. The insulation layer 358 is generally tubular in shape and surrounds the distal portion of the probe assembly 334. The probe electrode tip 356 remains exposed, however.

Partially embedded within the probe insulation 358 is a conductive shield 360 made of a conductive material such as a metal or a metal alloy. The shield 360 is substantially cylindrical, can be a solid layer or a wire mesh, and extends from adjacent to the distal end 353 of the probe 354 to within the trocar passage 341. Therefore, the shield 360 is embedded within the insulation 358 such that it does not contact the probe 354 but only an exposed portion 361 of the shield 360 protrudes from the insulation 358 within the trocar passage 341. The exposed portion 361 is contained within the trocar passage 341 and is located generally in the central portion of the probe assembly 334.

Pressing against the exposed portion 361 of the shield 360 is the conductive strip 335. The strip 335 remains in electrical contact with the shield 360 as the probe assembly 334 slides within the trocar passage 341. Correspondingly, the conductive strip 335 provides a conductive path from the shield 360 to the conductive portion 336 of the trocar assembly 332. Furthermore, a lead 362 connects the conductive portion 336 of the trocar assembly 332 to the return terminal of an electrosurgical generator.

Like the other embodiments described above, before the device 330 is used in an electrosurgical procedure, the trocar 332 is attached to a patient such that insulation 338 is located between the patient and the conductive guide 336. In addition, the patient's return electrode is in electrical contact with the patient and is also electrical connected to the electrosurgical generator return terminal. Likewise, the lead 362 extending from the trocar assembly 332 is connected to the generator return terminal. Finally, the generator output terminal is connected to the electrode probe 354.

During the electrosurgical procedure, the high frequency electrical current produced by the generator is passed through the probe 354 and is emitted from the probe tip 356. However, for the electrical current emanating from the tip 356 of the probe 354 the conductive guide 336 is not available as a resistive return path because of the insulation 338 located between the conductive guide 336 and the patient.

However, the high frequency electrical current passing through the probe 354 and the dielectric provided by the insulation 358 enshrouding the probe, results in an electrostatic field that is emitted radially substantially along the entire length of the probe. As the electrostatic field emanates from the probe 354, however, it strikes the conductive shield 360. Consequently, the field energy is absorbed by the shield 360 and conveyed, via the conductive strip 335, the conductive trocar portion 336, and the lead 362, into the return terminal of the generator. Therefore, any conductive elements positioned around the electrosurgical device 330 do not become capacitively coupled since the electrostatic field emanating from the probe 354 is absorbed by the conductive shield 360.

Furthermore, any portion of the field which comes into contact with the conductive guide 336 is absorbed by the guide and bled off. via lead 362, into the return terminal of the generator. Therefore, the trocar 332 does not become charged due to capacitive coupling because all electrostatic energy is bled off into the return terminal of the generator.

Figure 7:
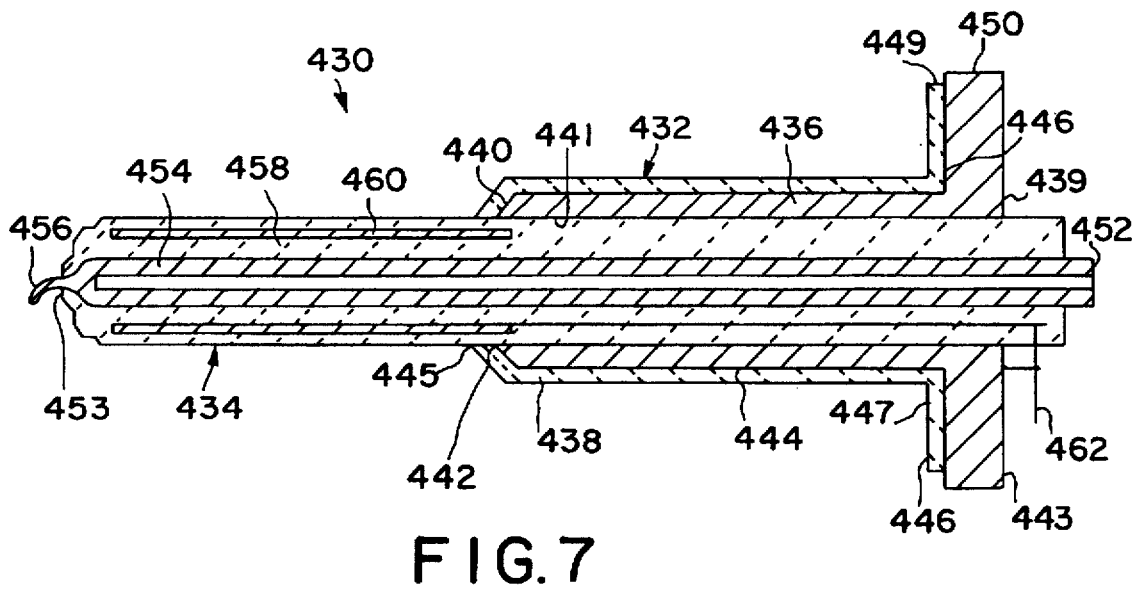
FIG. 7 is an enlarged cross-sectional side view of a further electrosurgical device in accordance with the present invention.

Referring to FIG. 7, an enlarged cross-sectional side view of a further embodiment of an electrosurgical device 430 in accordance with the present invention is depicted. The device 430 includes a trocar assembly 432 and a probe assembly 434.

The trocar assembly 432 has a conductive guide 436 which is partially surrounded by an insulation layer 438. The conductive guide 436 is made of a conductive material such as a metal or a metal alloy. Conversely, the insulation layer 438 is made of an insulating material such as a plastic or a ceramic.

The conductive guide 436 is generally tubular and has a probe receiving proximal end 439, an open distal end 440, and an open passage 441 extending therebetween. The open distal end 440 of the guide 436 is tapered to form a pointed tip 442 around the opening of the passage 441. Flange 443 extends radially outwardly from the probe receiving proximal end 439 of the guide 436.

Encasing the outside surface 444 of the conductive guide 436 is the insulation layer 438 which extends from the open distal end 440 of the conductive guide 436 to the flange 443. Correspondingly, the insulation layer 438 generally conforms to the shape of outer surface 444 including pointed end 445 and a flanged end 446 which abuts against the flange 443 of the conductive guide 436. As shown in FIG. 7, the outer diameter 449 of the insulation flange 447 is less than the outer diameter 450 of the conductive flange 443.

Received within the trocar assembly passage 441 is the probe assembly 434. The probe assembly 434 has a proximal end 452 and a distal end 453 which, respectively, protrude from the probe receiving proximal end 439 and the pointed end 445 of the trocar assembly 432. Extending along the center of the probe assembly 434 is a conductive probe 454. The probe 454 is generally tubular in construction, made of a conductive material such as a metal, a metal alloy, or the like, and has a curved electrode tip 456 protruding from the distal end 453.

Surrounding the probe 454 is an insulation layer 458. The insulation layer 458 can be a plastic material or a ceramic material having the appropriate dielectric properties. The insulation layer 458 extends from the distal end 453 of the probe assembly 434 substantially to the proximal end 452. Thus, only the probe tip 456 and the proximal end 452 of the probe 454 project from the insulation 458.

Embedded within the probe insulation 458 is a conductive shield 460 made of a conductive material. The shield 460 is substantially cylindrical and extends from adjacent to the distal end 453 of the probe 454 to within the trocar passage 441. The shield 460 is embedded within the insulation 458 such that the shield does not protrude from the insulation and does not come into electrical contact with the probe 454.

Attached to the shield 460 is a conductive lead 462. The lead 462 extends through the insulation 458 and also electrically connects to the conductive guide portion 436 of the trocar assembly 432. Correspondingly, the lead 462 provides a conductive path from the shield 460 to the trocar assembly 432. The lead 462 also connects to the return terminal of the electrosurgical generator.

As with the other embodiments described above, before the device 430 is used in an electrosurgical procedure, the trocar 432 is attached to a patient such that the flange 447 rests against the patient and thus provides insulation 438 between the patient and the conductive guide 436. In addition, the patient's return electrode is connected to both the patient and to the electrosurgical generator return terminal. Likewise, the lead 462 extending from the shield 460 and the trocar assembly 432 is connected to the generator return terminal. Finally, the generator output terminal is connected to the electrode probe 454.

During the electrosurgical procedure, the high frequency electrical current produced by the generator is passed through the probe 454 and is emitted from the probe tip 456. The conductive guide 436 is not available as a resistive return path for the electrical current emanating from the tip 456 of the probe 454 because of the insulation 438 located between the conductive guide 436 and the patient.

The high frequency electrical current passing through the probe 454 and the dielectric provided by the insulation 458 around the probe, results in an electrostatic field that is emitted radially along the entire length of the probe. As the electrostatic field emanates from the probe 454, however, it strikes the conductive shield 460. Consequently, the field energy is absorbed by the shield 460 and conveyed, via the lead 462, into the return terminal of the generator. Therefore, any conductive elements positioned around the electrosurgical device 430 will not become capacitively coupled inasmuch as the electrostatic field emanating from the probe 454 is absorbed by the conductive shield 460.

Furthermore, any portion of the field which comes into contact with the conductive guide 436 is absorbed by the guide and bled off, via lead 462, into the return terminal of the generator. Therefore, the trocar 432 does not become charged as a result of capacitive coupling because all electrostatic energy is bled off into the return terminal of the generator.

Figure 8:
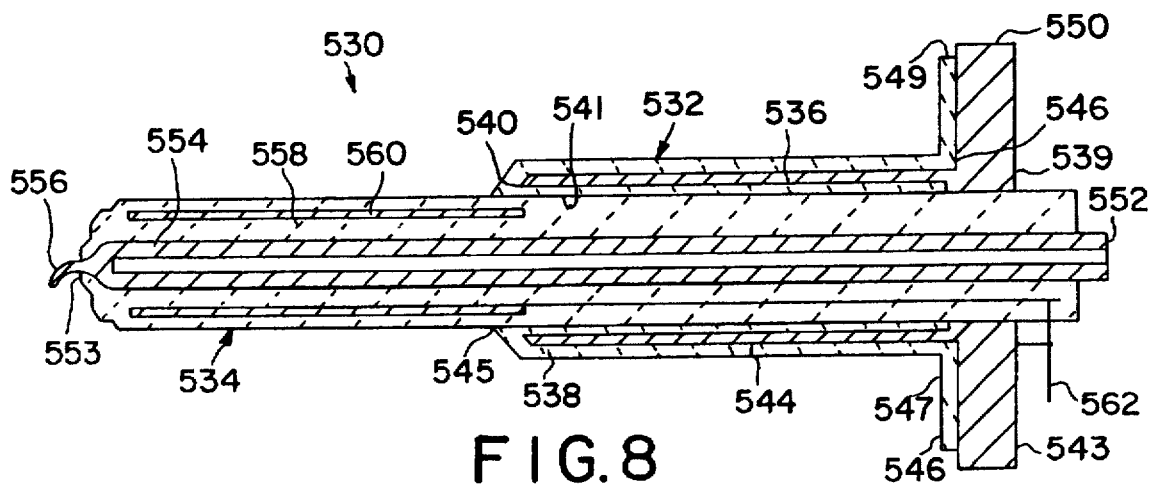
FIG. 8 is an enlarged cross-sectional side view of another electrosurgical device in accordance with the present invention.

Referring to FIG. 8, the electrosurgical device 530 is similar to the electrosurgical device 430 depicted in FIG. 7 except that the insulation layer 538 covers also the outer surface 544 of the conductive guide 536 and thus encases the conductive guide 536. In this manner, the trocar passageway 541 is insulated up to flange 543.

The portion of the insulation layer 538 within the passage 541 begins at the open distal end 540 of the guide and extends towards the probe receiving proximal end 539. The insulation layer 538 is generally tubular with a pointed end 545 and a flanged end 546 contiguous with the flange 543 of the conductive guide 536.

Figure 9:
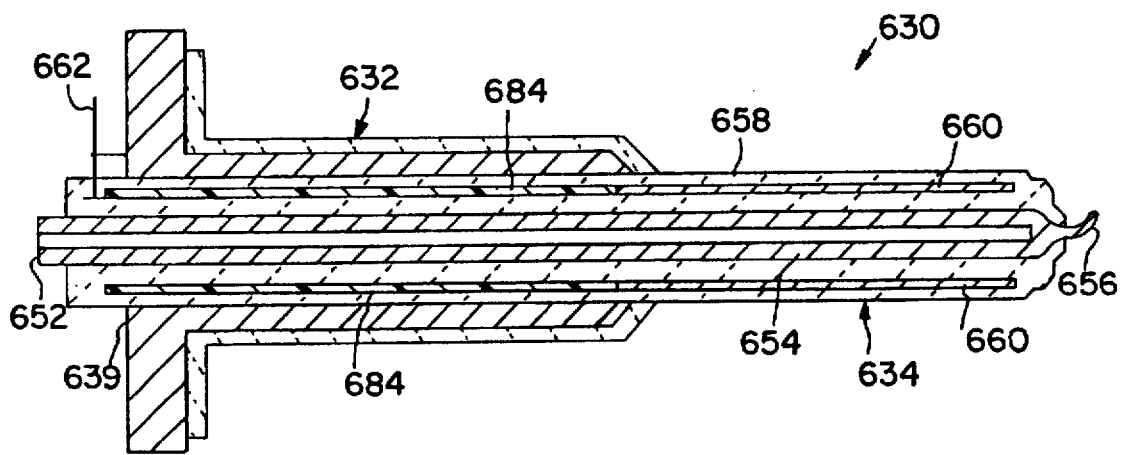
FIG. 9 is an enlarged cross-sectional side view of still yet another electrosurgical device that embodies the present invention.

Turning to FIG. 9, the electrosurgical device 630 is similar to the electrosurgical device 430 depicted in FIG. 7 except for a temperature sensitive thermistor buffer 684 within the insulation 658 that is electrically connected to and extends from the shield 660 toward the proximal end 652 of electrode 654.

The buffer 684 has substantially the same configuration as the shield 660. The buffer 684 is made from a semi-conductive composition which exhibits a decrease in resistance with an increase in temperature, i.e., has a negative temperature coefficient of resistance, and thus becomes more conductive as the probe heats up during use. The buffer 484 may be constructed of a semi-conductive carbon composition made from carbon powder mixed with a phenolic binder that is hot molded, or of a material having similar conductivity profile as a function of temperature.

Attached along the length of the buffer 684 is the conductive lead 662 which provides a conductive path for releasing the energy absorbed by the buffer 684.

The buffer 684 provides an additional means for absorbing electrostatic energy emanating from the probe 654.

Furthermore, the buffer 684 becomes more conductive, and thus absorbs more electrostatic energy, as the temperature of the probe assembly 634 increases due to an increase in the amount of electrical current being passed through the probe 654.

In FIGS. 1–9, it is preferred that the electrostatic energy radially emanating from adjacent to the proximal end of the probe to the distal end be absorbed by the conductive trocar, the shield, or both. Correspondingly, the probe assembly should not be extended so far from the trocar passage such that electrostatic energy can freely escape through a gap between the conductive trocar and the shield. Therefore, as shown in FIGS. 1–9, the shield always extends within the passage provided by the conductive guide portion of the trocar.

It will be readily apparent from the foregoing detailed description of the invention and from the illustrations thereof that numerous variations and modifications may be effected without departing from the true spirit and scope of the novel concepts or principles of this invention.

I claim:

1. An electrosurgical device comprising:

a trocar assembly having a conductive guide portion defining an open passage with a probe receiving proximal end and an insulated portion defining an open distal end and extending into said open passage;

a probe assembly slidably received within said passage and having a conductive probe with a proximal end and a distal end, an insulation layer surrounding said probe and extending from said distal end, and a conductive shield attached to said insulation layer and surrounding said probe; and means conductively connecting said conductive shield on said probe to said conductive guide portion of said trocar.

2. The electrosurgical device of claim 1, wherein said shield is embedded within said insulation layer.

3. The electrosurgical device of claim 1, wherein said shield includes an exposed portion which extends from said insulation layer.

4. The electrosurgical device of claim 1, wherein said conductive guide portion has an outer surface with said insulated portion disposed thereon.

5. The electrosurgical device of claim 1, wherein said conductive guide portion has a distal end with said insulated portion attached thereto.

6. The electrosurgical device of claim 1, further including a flange extending radially outwardly from said insulated portion.

7. The electrosurgical device of claim 6, further including threads located on said insulated portion and adjacent to said flange.

8. The electrosurgical device of claim 1, further including a cap attached to said conductive guide portion, said cap having an open bore and said probe extending therethrough.

9. The electrosurgical device of claim 1, further including a channel etched within said insulated portion.

10. The electrosurgical device of claim 1, wherein said connecting means includes a conductive strip attached to said conductive guide portion.

11. The electrosurgical device of claim 1, wherein said connecting means includes a lead attached to said shield and said conductive guide portion.

12. An electrosurgical device comprising:

a trocar assembly having a conductive guide portion defining an open passage with a probe receiving proximal end and an insulated portion defining an open distal end;

a probe assembly slidably received within said passage and having a conductive probe with a proximal end and a distal end, an insulation layer surrounding said probe and extending from said distal end, and a conductive shield attached to said insulation layer and surrounding said probe;

means conductive connecting said conductive shield on said probe to said conductive guide portion of said trocar, said means including a lead attached to said shield and said conductive guide portion; and a temperature sensitive thermistor buffer within said insulation layer and electrically connected to said lead.

13. An electrosurgical device comprising:

a trocar assembly having a conductive guide portion defining an open passage and an insulated portion attached to said conductive guide portion and extending into said open passage;

a probe assembly slidably received within said passage and having a cylindrical conductive probe, an insulation layer surrounding said probe, and a cylindrical conductive shield integral with said insulation layer;

means for conductively connecting said conductive shield to said conductive guide portion.

14. The electrosurgical device of claim 13, wherein said shield is completely embedded within said insulation layer.

15. The electrosurgical device of claim 13, wherein said shield includes an exposed portion which extends from said insulation layer.

16. The electrosurgical device of claim 13, wherein said conductive guide portion has an outer surface with said insulated portion disposed thereon.

17. The electrosurgical device of claim 13, wherein said conductive guide portion has a distal end with said insulated portion attached thereto.

18. The electrosurgical device of claim 13, further including a cap attached to said conductive guide portion, said cap having an open bore and said probe extending therethrough.

19. The electrosurgical device of claim 13, wherein said connecting means includes a conductive strip attached to said conductive guide portion.

20. The electrosurgical device of claim 13, wherein said connecting means includes a lead attached to said shield and said conductive guide portion.

21. An electrosurgical device comprising:

a trocar assembly having a conductive guide portion defining an open passage and an insulated portion attached to said conductive guide portion;

a probe assembly slidably received within said passage and having a cylindrical conductive probe, an insulation surrounding said probe, and a cylindrical conductive shield integral with said insulation layer;

means for conductively connecting said conductive shield to said conductive guide portion, said means including a lead attached to said shield and said conductive guide portion; and a temperature sensitive buffer within said insulation layer and attached to said lead.

* * * * *